United States Patent
Åberg (12)

(10) Patent No.: US 6,656,876 B1
(45) Date of Patent: Dec. 2, 2003

(54) SQUARIC ACID ACTIVATED CARRIER USABLE FOR IMMOBILIZATION OF COMPOUNDS CONTAINING AMINE GROUPS

(75) Inventor: Per-Mikael Åberg, Uppsala (SE)

(73) Assignee: Amersham Biosciences AB, Uppsala (SE)

( * ) Notice: Subject to any disclaimer, the term of this patent is extended or adjusted under 35 U.S.C. 154(b) by 0 days.

(21) Appl. No.: 09/807,463

(22) PCT Filed: Oct. 14, 1999

(86) PCT No.: PCT/SE99/01861

§ 371 (c)(1),
(2), (4) Date: May 22, 2001

(87) PCT Pub. No.: WO00/23478

PCT Pub. Date: Apr. 27, 2000

(30) Foreign Application Priority Data

Oct. 16, 1998 (SE) ................................................ 9803565
Oct. 19, 1998 (SE) ................................................ 9803588

(51) Int. Cl.[7] .......................... B01J 20/36; C07K 17/06; C12N 11/06; C12N 11/10
(52) U.S. Cl. ..................... 502/402; 252/179; 424/179.1; 435/178; 435/181; 435/810; 502/404; 516/100; 516/101
(58) Field of Search .......................... 252/179; 435/178, 435/181, 810; 502/402, 404; 424/179.1; 516/100, 101

(56) References Cited

U.S. PATENT DOCUMENTS

| 3,725,291 | A | * | 4/1973 | Serbus et al. ........... 252/179 X |
| 5,089,391 | A | * | 2/1992 | Buechler et al. ........ 435/810 X |
| 5,942,406 | A | * | 8/1999 | Burton et al. ........... 435/178 X |
| 6,277,782 | B1 | * | 8/2001 | Moller et al. ............... 502/402 |
| 6,426,315 | B1 | * | 7/2002 | Bergstrom et al. ...... 502/402 X |
| 6,602,692 | B1 | * | 8/2003 | Glüsenkamp et al. ....... 435/181 |

FOREIGN PATENT DOCUMENTS

WO      WO 9515983      6/1995

OTHER PUBLICATIONS

Glüsenkamp, K., et al. "Squaric Acid Diethylester: A Simple and Convenient Coupling Reagent" Z. Naturforsch, 46c, 1991, pp. 498–501.
Tietz, L., et al. "Conjugation of p–Aminophenyl Glycosides with Squaric Acid Diester to a Carrier Protein and the Use of Neoglycoprotein in the Histochemical Detection of Lectins 1" Bioconjugate Chem., vol. 2, 1991, pp. 148–153.

* cited by examiner

Primary Examiner—Richard D. Lovering
(74) Attorney, Agent, or Firm—Royal N. Ronning, Jr.; Stephen G. Ryan

(57) ABSTRACT

A storage stable composition comprising a carrier usable for the immobilization of compounds containing an amine group, for instance biomolecules and/or affinity ligands. The carrier has been activated to exhibit a squaric acid derivative linked to the carrier and is placed in contact with an aqueous medium. A kit comprising the storage stable composition is also disclosed.

11 Claims, 1 Drawing Sheet

US 6,656,876 B1

SQUARIC ACID ACTIVATED CARRIER USABLE FOR IMMOBILIZATION OF COMPOUNDS CONTAINING AMINE GROUPS

This application is a 371 of PCT/SE99/01861 filed Oct. 14, 1999.

The present invention relates to storage stable, activated carrier in the form of matrices including surfaces. In particular it relates to such matrices suitable as carrier to which compounds containing an amine group may be covalently bound.

The invention also relates to a kit comprising such activated carrier, the kit being shippable to customers by virtue of the long term stability of said carrier.

In the context of this description of the invention the words carrier/carriers, matrix/matrices and medium/media are used interchangeable, if not otherwise said.

BACKGROUND OF THE INVENTION

The immobilization of biomolecules on various carriers finds great utility in research and industry, and many methods have been disclosed in the literature. These methods comprise an activation of a carrier, e.g. a matrix in the form of a gel, a surface of a polymer bead etc. The activation process generally comprises subjecting the carrier to a reactive agent that reacts with —OH groups or amine groups on the carrier, thereby, either directly or subsequent to further steps, forming intermediate reactive structures/sites. These structures may then be reacted with the compound in question, thereby immobilizing the compound.

Illustrative examples of such methods are the CNBr method, and epoxy activation. The activated intermediates obtained by these methods must be freeze dried in order to be shippable to customers. Freeze drying is fairly complicated and in addition require processing at the customer before the freeze dried intermediates can be used.

These and other activation and immobilization methods are described in "Immobilized affinity ligand techniques" by G. T. Hermanson, Academic Press, 1992.

In WO 95/15983 (Glüsenkamp et al) there is disclosed a process for immobilizing biomolecules and affinity ligands on carriers. This process comprises reacting an aminated polymer carrier with a bifunctional electrophilic squaric acid derivative as activating agents to form an activated intermediate (activated matrix or activated media or activated carrier), and coupling a biomolecule to the activated carrier.

For most of the above-mentioned activation processes it has been commonly known that the activated carriers are relatively unstable towards hydrolysis. Remembering that commercially available activated carrier media should have as long shelf time as possible, for instance from one up to several months, it is no surprise that commercial products comprising activated matrices typically have been sold in form of lyophilized compositions. For squarate activated carrier media we are not aware of any commercial products differing from what has been said above. When looking into the scientific literature it appears that most synthetic routes in which squarate activated material are obtained typically end up in crystallized and/or dried material. In the alternative the activated material is used more or less directly upon synthesis. See for instance Kamath et al., Glycoconjugate J. 13 (1996) 315–319; and Ola Blixt, Thesis: Enzymatic solid phase synthesis of carbohydrates, Swedish University of Agricultural Sciences, Uppsala, Sweden (1999) (see in particular page 50); DE 4341524 (Glüsenkamp et al); and DE 19624990 (Glësenkamp et al). An investigation of the hydrolysis of soluble squarate activated materials (monoamides) has been published (Glësenkamp et al., Z. Naturforsch. 46c (1991) 498–501). The storage of squarate activated aminated matrices moistured with methanol or in ethanol atmosphere has been described in the experimental part of WO. 9515983 (Glësenkamp et al). The reactivity is expected to be retained during these storing conditions because reaction with methanol and ethanol, respectively, will only mean a transesterification retaining the ester status of the activated group and thus also maintaining its reactivity.

It would be advantageous to provide a commercial product in form of an activated carrier comprising reactive squaryl groups said activated carrier being dispensed in aqueous media and having a shelf life of from 1–2 months up to several months without showing any significant loss in activity. This is in particular true in case the use is for immobilizing water-soluble compounds to the activated medium, for instance amine-containing biomolecules such as proteins. The aqueous media is typically an aqueous liquid.

It would also be advantageous in case such storage stable compositions would be resistant towards microbial growth.

Other publications connected to squarate activated materials are Tietze et al., Chem. Ber. 124(5) (1991) 1215–1221; Tietze et al., Bioconjugate Chem 2 (1991) 148–153; H ällgren et al., J. Carbohydrate Chem. 14(4&5) (1995) 453–46; Ausanneau et al., Bioorganic & Medicinal Chemistry 4 (1996) 2003–2010; and Pozsgay et al., J. Org. Chem. 62 (1997) 2832–2846.

SUMMARY OF THE INVENTION

The object of the present invention is therefore to provide a storage stable activated carrier comprising reactive squaryl groups, said carrier being dispersed in an aqueous medium for use in the immobilization of nucleophilic compounds, typically amine containing compounds. The activated medium should be stable during storage and/or resistant against bacterial growth over extended periods of time.

For the purpose of the invention the term "activated medium" or "activated carrier" or "activated matrix" mean a carrier to be used as a carrier for a nucleophilic compound. Said carrier has been provided with reactive squaryl groups enabling easy coupling of said compound to said carrier. The activated carrier should be regarded as an intermediate in the process of making immobilized forms of said compounds.

Nucleophilic compounds that are contemplated in the context of the invention typically contain a primary and/or a secondary amine group, for instance proteins or other compounds exhibiting peptide structure or other biomolecules and other organic compounds exhibiting this type of amine groups.

The inventor has now surprisingly discovered that a carrier as defined above comprising amine groups activated with an electrophilic squaric acid derivative may be stable in aqueous media. Unexpectedly it has been recognized that the rate of hydrolysis of reactive squarate groups bound; to carriers is sufficiently slow for enabling storage of the activated carriers in aqueous media.

Thus, in accordance with the present invention there is provided a storage stable composition comprising a carrier as defined above and usable for the immobilization of nucleophilic compounds. The carrier comprises primary or secondary amino groups that have been activated to carry reactive squaric acid derived groups linked to said primary or secondary amine sites on said carrier, said carrier being in contact with an aqueous medium, e.g. an aqueous liquid.

In a second aspect of the invention there is provided a method of preparing such a composition. This method is defined in claim 11.

Furthermore, in accordance with the invention there is provided a kit for storing the composition over extended periods of time, this being defined in claim 10.

The composition according to the present invention is stable for an extended period of time as defined above, for instance for a week, a month or even longer periods of time, such as two, three or more months.

Preferred embodiments are defined in the dependent claims.

DETAILED DESCRIPTION OF THE INVENTION

The squaric acid derivatives useful for making the activated carriers may be selected among bifunctional electrophilic squaric acid derivatives, such as dialkoxyesters (e.g. dimethylester, diethylester, dibutylester and also corresponding mixed diester (squarates)), dihalides and diimidazolides. Other reactive derivatives may also be used. The activation reaction is normally run in inert media. See Gl üsenkamp WO9515983. In case the reactive group formed on the carrier is too reactive to be stored in the contemplated aqueous media, it may be easily transformed to a group of lower reactivity. For instance, in case a squaric acid dihalide is used to prepare the activated carriers, the formed monohalide group may be transformed to the corresponding ester function, for instance by running the reaction in the presence of an alcohol.

A reactive intermediate according to the invention may be represented by the general formula

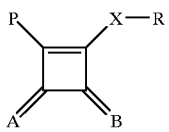

wherein
represents a matrix (carrier) containing primary and/or secondary amine groups binding to the squaric acid derived structure (squaryl group, e.g. squarate structure) which in turn constitutes the reactive group in the formula above. There are often several reactive squaric acid derived groups (e.g. squarate groups) on one and the same matrix P.

A and B independently of each other can be O or S;

X can be O or S; and

R may represent an inert organic group that together with X and the squaryl group forms an electrophilic structure.

R is, for instance, a $C_1$ to $C_{30}$ hydrocarbon group comprising one or more straight, branched or cyclic hydrocarbon chains that may be broken at one or more locations by a thioether sulphur or an ether oxygen and/or substituted with one or more R'O- groups where R' is hydrogen and/or $C_1$ to $C_6$ alkyl or corresponding sulphur analogues (R'S-). The preferred Rs are $C_1$ to $C_6$ alkyl, such as methyl, ethyl, n-propyl, isopropyl, and possibly also isoforms of butyl. Preferably there are at most one O or S atom on each carbon atom in R.

R may also be an imidazolide group or another group resulting in the squarate structure in the general formula being a reactive electrophilic squarate group on the carrier. In this case the stability of the activated carrier shall be comparable to the stability of the squaric acid mono amide mono alkyl ester groups defined above (R=alkyl).

By the term "inert" is meant that R does not contain any group that adversely affect the reactivity of the activated squaryl group shown. Destabilizing groups in R may for instance be primary and secondary amines.

By the term "stable" is meant that the ability to react with primary and secondary amines is retained for a prolonged time without being significantly or irreproducibly decreased. This in turns means that the activated intermediate can be stable even if the activated intermediate participate in transesterifications with alcohol groups present in the storage media, the carrier or the inert group R.

As carriers to be activated with squaric acid derivatives defined above, matrices exhibiting primary and/or secondary amine groups can be used.

The term "matrix" is to be understood to encompass any physical form such as particles, monoliths, fibers, membranes, tube walls, capillaries, surfaces etc. The matrix may be porous or non-porous and soluble, insoluble or insolubilizable in aqueous media or other liquids.

In the preferred modes of the invention the matrix is based on a polymer that exposes a hydrophilic surface to the aqueous media used, i.e. expose hydroxy (—OH), carboxy (—COOH), carboxamido (—$CONH_2$, possibly in N-substituted forms), amino (—NH2, possibly in substituted form), oligo- or polyethylenoxy groups on their external and, if present, also on internal surfaces. Typically the matrix is of the same kind as those normally used as chromatographic matrices. The polymer may, for instance, be based on polysaccharides, such as dextran, starch, cellulose, pullulan, agarose etc., which if necessary have been cross-linked, for instance with bisepoxides, epihalohydrins, 1,2,3-trihalo substituted lower hydrocarbons, to provide a suitable porosity and rigidity. The matrix may also be based on synthetic polymers, such as polyvinyl alcohol, poly hydroxyalkyl acrylates, poly hydroxyalkyl methacrylates, poly acrylamides, polymethacrylamides etc. In case of hydrophobic polymers, such as those based on divinyl and monovinyl substituted benzenes, the surfaces of the matrix are often hydrophilized to expose hydrophilic groups as defined above to a surrounding aqueous liquid.

The matrices may also be of inorganic nature, e.g. silica, zirconium oxide etc.

If the matrices as such do not exhibit amine functionality they may be derivatized by methods known by the man skilled in the art to do so.

The activating method is fully described in the referenced WO-publication, and will not be discussed herein.

The storage medium for the intermediates in question is aqueous, typically in form of an aqueous liquid. It preferably comprises an antibacterially active component. This component preferably is selected form organic solvents suitably miscible with water.

A preferred class of components is alcohols, in particular alkanols, such as methanol, ethanol, propanol, iso-propanol, butanol, sec-butanol, tert-butanol. The most preferred alcohol is ethanol.

The amount of the antibacterial component needed is an amount sufficient for preventing bacterial or microbial growth in the composition.

The composition of the aqueous medium may comprise water in an amount of 5–100%, preferably 20–95%, more preferably 40–85%. The amount of organic solvent suitably miscible with water is in the interval 5–95%, preferably 5–80%, more preferably 10–60% such as 25–60. Volume-% (v/v) is contemplated. The organic solvent is preferably a water-miscible alcohol.

The pH of the aqueous medium may be in the range 5–9. Standard buffer systems that do not adversely affect the stability may be used, e.g. 0.3 M borate buffer. Amine buffers, in particular adjusted to pH below 1 minus their pKa should be avoided.

When being used the activated carrier is contacted with an organic compound containing an amine group under conditions permitting binding of the amine compound to the carrier via a newly formed squarate amide structure. The compound containing the amine function is preferably a bioorganic molecule. Typically the amine compound is a member of a so-called affinity pair. Examples of affinity pairs are antigen/hapten—antibody, carbohydrate structure—lectin, complementary nucleic acid sequences and any other native or synthetic ligand-receptor pair in which the ligand and receptor are able to cling to each other via affinity. One special class of affinity pairs has biological origin. They are consequently called bioaffinity pairs.

BRIEF DESCRIPTION OF DRAWING

The invention will now be described in detail by way of examples and with reference to Scheme A and FIG. 1.

Scheme A:

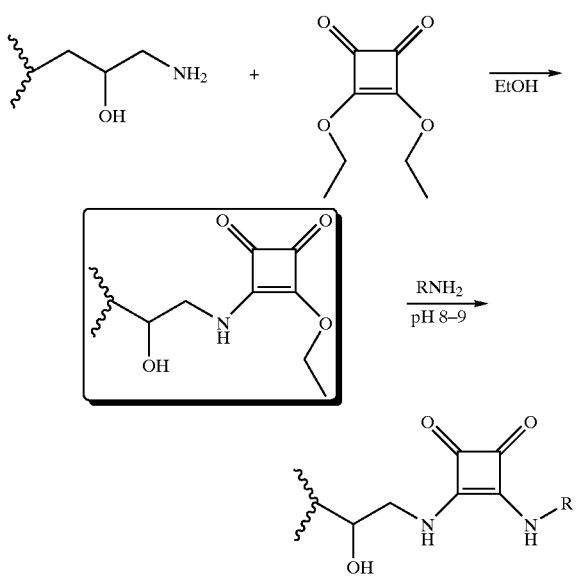

Figure 1:
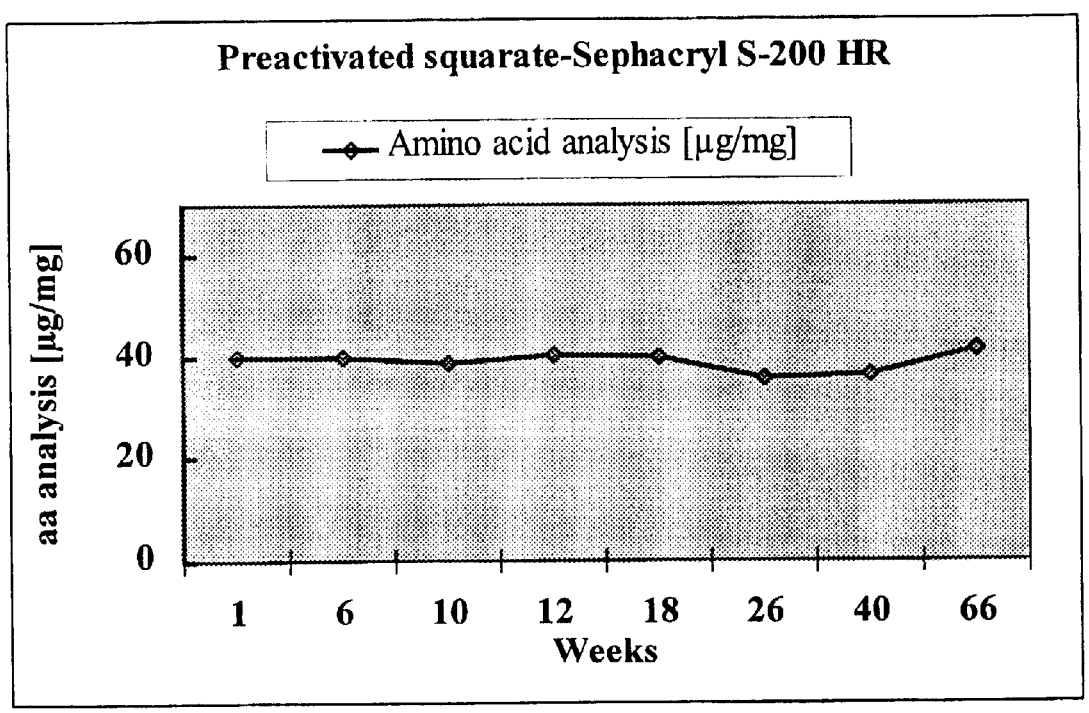

In scheme A, $RNH_2$ is the compound to be immobilized to the matrix. The scheme is focusing on one kind of introduced amino groups. The reaction will in principle be the same for the other amino groups.

FIG. 1 gives a graph showing the long-term stability of a composition according to the invention. The amino acid analysis data shown correspond to coupling yields of 75–85%. We have immobilized other ligands with similar or higher yields.

EXAMPLE 1

Preparation of Amine Containing Beads

Polymer beads (Sephacryl S-200, Amersham Pharmacia Biotech AB, Uppsala, Sweden) were amine functionalized in the following way.

Epoxy activated beads were washed with water and drained, and then added to a reaction vessel and an equal volume of 1 M $NH_3$ was added to the vessel. The vessel was sealed and circle shaken in a water bath at 50° C. for 23 h. The beads were washed with water (>10×gel volume) and stored in 20% ethanol in water at +2–+8° C.

After amination the beads will contain different amino groups —$CH_2CHOHCH_2NH_2$ (obtained by reaction of ammonia with epoxy groups), —$NHCOCH_2CHNH_2$ (obtained by reaction of ammonia with acrylamido groups and corresponding crosslinking groups obtained via further reaction with epoxy and acrylamido groups.

EXAMPLE 2

Activation of Aminated Matrix with 3,4-Diethoxy-squarate

The amine functionalized Sephacryl (100 ml, from Example 1) stored in 20% EtOH, was washed with absolute ethanol (10×1 gel volumes). The beads were added to a flask with screw cap. An equal volume of absolute ethanol was added followed with benzyl alcohol (ca 250 μl/50 ml ethanol) and the squarate (ca 1.5–2 equivalents compared to the amine contents of the beads). The reagents were mixed and a small sample of the liquid phase, used as reference for HPLC, was taken out immediately. The flask was shaken in a water-bath at 20–60 ° C. The progress of the reaction was followed by HPLC by taking out small samples of the liquid phase, after regular intervals, dilute 50 times with EtOH (30 μl in 1.5 ml) and analyze on a Shimadzu HPLC. Benzyl alcohol was used as an internal standard in the HPLC analysis. The substitution degree was assumed to be approximately equal to the consumed amount of the squarate reagent.

The beads were washed with ethanol 99.5% followed with 20% ethanol. The activated beads were divided in 10 ml samples slurried in 20% ethanol and stored at 2–8° C.

EXAMPLE 3

Coupling of Porcine Trypsin

The activated beads, stored in 20% EtOH, were washed with water (ca 5×1 gel volume, gv), followed with a borate buffer 0.3M borate 1.5 M $Na_2SO_4$, pH 9. The enzyme solution was made by dissolving 100 mg Porcine trypsin in ca 10 ml 0.5 M Na2SO4 and 0.3 M borate buffer pH 9 which was added to the beads The mixture was shaken at room temperature for 6 hrs. The beads were washed with tris buffer (0.1 M, 0.5 M NaCl, pH 8) 4×1 gel volumes. Followed, alternatively four times with tris and acetate buffer (0.1 M, pH 5), and finally with water five times. Stored in 20% EtOH.

EXAMPLE 4

Stability Test

Stability tests on the intermediates in the storage mode according to the present invention (the storage medium used in the examples is 20% ethanol in water, temperature 2–8° C.) were made by taking samples of the intermediates at irregular intervals during 66 weeks (more precisely at 1, 6, 10, 12, 18, 26, 40 and 66 weeks).

These samples were used for immobilization of porcine trypsin on the matrix according to example 3. The substitution degree was investigated by amino acid analysis.

FIG. 1 shows the results from the storage test. From this figure it can be concluded that within the experimental errors, the intermediates are stable in the aqueous storage medium over an extended period of time, i.e. at least about 66 weeks.

The composition according to the invention is suitably prepared by replacing the liquid reaction medium from the activated carrier medium, for instance by washing, with the aqueous medium that ultimately will be used for storing the composition.

The composition is delivered to the customer as a kit comprising a storage container containing the composition, i.e. the activated medium in contact with the aqueous medium. Such storage means can comprise bottles, ampoules, flasks, and other closed vessels not permitting evaporation. In case of carrier media in the form of open surfaces (e.g. wells of a microtiter plate), and monolithic porous and nonporous matrices, strips and the like, the medium itself may function as the storage means, provided there is an appropriate cover means preventing evaporation from the activated surface.

What is claimed is:

1. A storage stable composition comprising a carrier medium exhibiting primary and secondary amine groups and usable for the immobilization of amine group containing compounds, said carrier medium being activated to exhibit electrophilic squaric acid derived groups linked to said medium, said carrier medium being in contact with an aqueous medium, said composition being comprised in a closed vessel not permitting evaporation of said aqueous medium.

2. The composition of claim 1, wherein said activated carrier medium is represented by the formula

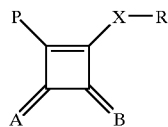

wherein
P represents said carrier;
A and B independently of each other can be O or S;
X can be O or S; and
R represents and inert organic group that together with X and the squaryl group forms an electrophilic structure.

3. The composition of claim 1, further comprising an antibacterially active component.

4. The composition of claim 3, wherein the antibacterially active component is a solvent miscible with water.

5. The composition of claim 1, wherein said aqueous medium comprises water in an amount of 5–100%.

6. The composition of claim 1, wherein said aqueous medium comprises an alcohol in an amount of 5–95%.

7. The composition of claim 1, which is stable for at least one week.

8. The composition of claim 1, wherein said carrier medium is in the form of beads.

9. The composition of claim 1, wherein the pH of the aqueous medium is 5–9.

10. A kit comprising a means for storing a composition as claimed in claim 1, and such a composition contained in said storage means.

11. A method of making a storage stable composition comprising a matrix carrying reactive electrophilic squaryl groups, said method comprising
i) reacting a matrix comprising primary and/or secondary amine groups with a bifunctional nucleophilic squaric acid derivative thereby introducing squaryl groups on the matrix to give an activated matrix
ii) washing the activated matrix with an aqueous medium; and
iii) storing said activated matrix in said aqueous washing medium for at least a week.

* * * * *